United States Patent

Palumbo et al.

Patent Number: 6,107,539
Date of Patent: Aug. 22, 2000

[54] DISPOSABLE ABSORBENT ARTICLES HAVING REDUCED SURFACE WETNESS

[75] Inventors: Gianfranco Palumbo, Bad Homburg; Mattias Schmidt, Idstein; Manfred Plischke, Steinbach/Ts.; Wolfgang Meyer, Florsheim, all of Germany

[73] Assignee: The Procter & Gamble Company, Cincinnati, Ohio

[21] Appl. No.: 09/068,779

[22] PCT Filed: Oct. 22, 1996

[86] PCT No.: PCT/US96/17001

§ 371 Date: May 14, 1998

§ 102(e) Date: May 14, 1998

[87] PCT Pub. No.: WO97/17923

PCT Pub. Date: May 22, 1997

[30] Foreign Application Priority Data

Nov. 14, 1995 [EP] European Pat. Off. .............. 95117922

[51] Int. Cl.[7] ...................................................... A16F 13/15
[52] U.S. Cl. ...................... 604/378; 604/385.1; 604/381; 604/367; 604/358
[58] Field of Search ...................................... 604/358, 367, 604/378, 381

[56] References Cited

U.S. PATENT DOCUMENTS 5,360,420 11/1994 Cook et al. .............................. 604/378
5,364,382 11/1994 Latimer et al. .......................... 604/378

Primary Examiner—John G. Weiss
Assistant Examiner—Paul A. Shanoski
Attorney, Agent, or Firm—Kevin D. Hogg; Steven W. Miller; Jacobus C. Rasser

[57] ABSTRACT

A disposable absorbent article comprising a backsheet, a topsheet, a fluid acquisition/distribution region and at least on fluid storage region, said article having a total product acquisition performance of more than 3.75 ml/sec in the first gush and more than 0.5 ml/sec in the fourth gush and an in bag stack height of less than 9.9 mm, characterized in that said topsheet allows to retain no more them 0.25 g of fluid as measured by the topsheet-on-acquisition-material-wetness test, and that said acquisition/distribution region has a drip capacity of at least 5.0 grams of fluid per gram of material.

21 Claims, 2 Drawing Sheets

DISPOSABLE ABSORBENT ARTICLES HAVING REDUCED SURFACE WETNESS

The present invention relates to disposable absorbent articles such as diapers, incontinence articles, sanitary towels, training pants and the like, such articles having good fluid handling properties and reduced tendency for surface wetness.

BACKGROUND OF THE INVENTION

Disposable, absorbent articles such as diapers, incontinence articles, sanitary towels, training pants and the like are well know in the art. Typically, disposable absorbent articles comprise a liquid pervious topsheet that faces the wearers body, a liquid impervious backsheet that faces the wearers clothing, and an absorbent core interposed between the liquid previous topsheet and the backsheet. The absorbent core must often be capable of absorbing and handling relatively large volumes of fluid like urine or other exudates discharged from the body of the wearer, and especially relatively large fluid volumes discharged over relatively short periods of time. The absorbent core needs to be capable of acquiring, distributing, and storing discharges initially deposited on the topsheet of the absorbent article. Preferably the design of the absorbent core is such that the core acquires the discharges substantially immediately after they have been deposited on the topsheet of the absorbent article, with the intention that the discharges do not accumulate on or run off the surface of the topsheet, since this may result in inefficient fluid containment by the absorbent article which may lead to wetting of outer garments and discomfort for the wearer. In addition, preferably the absorbent core will have a design that facilitates the initially retained discharges to be transported away from the area of initial retention to the ultimate storage region, which should not become prematurely saturated and so that bulk of the absorbent material in the storage core is utilised effectively.

There have been many attempts to design absorbent articles or cores to improve the above requirements, in particular when further requirements were brought up with respect to a desired reduction of product bulkiness or thickness.

In particular, substantial effort has been spent against improving the fluid handling properties of the absorbent cores by adding fluid acquisition enhancing materials thereto.

Several patent publications deal with improvements of fluid handling performance by adding specially treated cellulosic material.

For example U.S. Pat. No. 4,898,642 of Moore et al. discloses special twisted, chemically stiffened cellulosic fibres and absorbent structures made therefrom.

EP 0 640 330 of Bewick-Sonntag et al. discloses the use of such fibres in a specific arrangement with specific superabsorbent materials.

EP 0 397 110 (Latimer) discloses an absorbent article comprising a surge management portion for improved fluid handling, having specific basis weights, acquisition times and residual wetness.

EP 0 359 501 (Cadieux) discloses an absorbent structure in general by exemplifying a feminine hygiene product with

- a hydrophilic cover layer (in direct contact with the wearer) with low density and large porosity;
- a transfer layer with higher density, smaller pores;
- and a reservoir layer such that gradients (continuous or stepwise) are generated; and such that fluid passes well between the regions.

Both-cover and transfer region tend to avoid fluid dispersion, but rather enhance transfer of the fluid to the next layer, whereas the reservoir layer also distributes.

EP 0 312 118 (Meyer) discloses an absorbent article with a fibrous topsheet with larger pores than the pores of the underlying transport layer, which in turn has lager pores than the underlying absorbent body. Further, the transport layer has to have a hydrophilicity which is less than the one of the absorbent core, and may generally be characterised as being substantially hydrophobic.

In EP 0 312 118 it is said that some liquid might remain in the transport layer and also the topsheet, so as to cause a wet feel on the surface. In order to overcome this problem, it is proposed in EP 0 312 118 to exploit the resilient compressibility of the transport layer, such that in use under the pressure exerted by the baby, the pores become smaller and then can dry out the topsheet and transport the fluid away.

The above prior art structures, however, while exhibiting an improved acquisition performance of the core, still suffer from a wet and damp feel on the surface of the total structures (i.e. on the topsheet), due to (in absolute measurements) small amounts of liquid remaining loosely bound in the topsheet, which however, are clearly identified by consumers negatively as "wet feel".

There is also the need to further improve the fluid handling properties of the total structure, in particular when moving to thinner products which often comprise high amounts of superabsorbent particles dispersed in relatively small amounts of fluff. Fluid acquisition and distribution properties indeed can suffer from relative lack of void spaces as well as from high superabsorbent concentrations.

Hence it is the object of the current invention, to provide absorbent cores allowing for a reduced amount of loosely bound fluid in the topsheet and resulting in a drier feel of the topsheet.

It is a further object of the invention, to enhance fluid acquisition properties of the absorbent cores even beyond existing structures, while not compromising on the topsheet dryness.

SUMMARY OF THE INVENTION

In order to achieve the ultimate goal of good skin dryness of the wearer together with good leakage performance through good fluid acquisition and storage functionality of the article even at repeated gushes, the uppermost material, which is directed towards the wearer's skin, has to be drained very effectively and a minimum of loosely bound liquid should remain in this layer.

In broadest technical terms, the invention aims at improving the hydraulic suction from the topsheet into the absorbent core structure underneath the topsheet layer. This can be achieved by careful selection of topsheet and acquisition/distribution materials according to specific parameter as outined later on.

In particular, this is achieved by a disposable absorbent article comprising a backsheet, a topsheet, a fluid acquisition/distribution region and at least one fluid storage region, said article having a total product acquisition performance of more than 3.75 ml/sec in the first gush and more than 0.5 ml/sec in the fourth gush and an in bag stack height of less than 9.9 mm, characterised in that said topsheet allows to retain no more than 0.25 g of fluid as measured by the topsheet-on-acquisition-material-wetness test, and that said acquisition/distribution region has a drip capacity of at least 5.0 grams of fluid per gram of material.

DETAILED DESCRIPTION

Absorbent Articles

As used herein, the term "absorbent articles" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner).

An absorbent article generally comprises
an absorbent core (which may consist of sub-structures);
a fluid pervious topsheet;
a fluid impervious backsheet;
optionally further features like closure elements or elastification.

Figure 1:
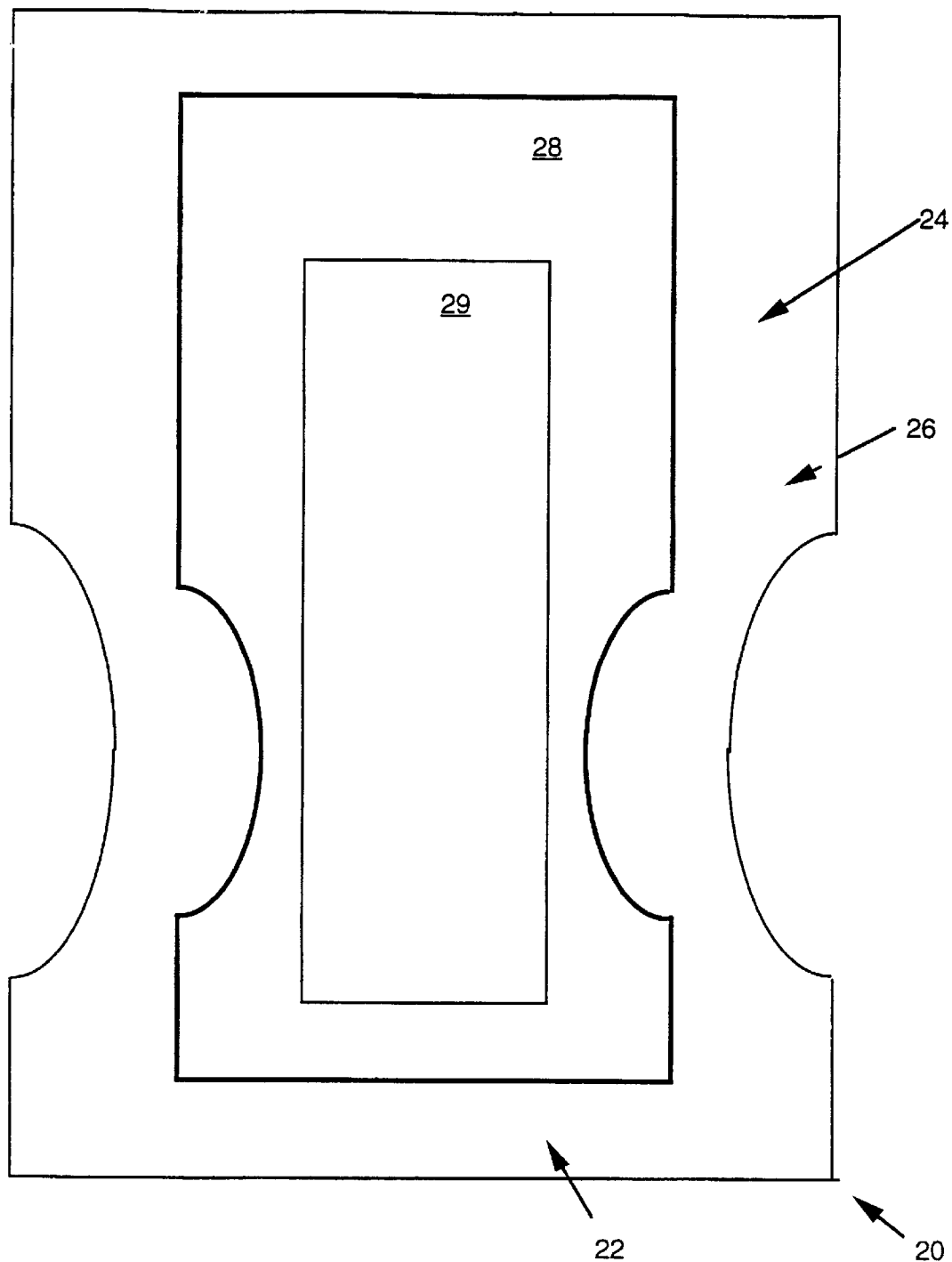
FIG. 1 shows a specific embodiment of an absorbent article by schematically representing a disposable baby diaper.

A specific embodiment of an absorbent article of the present invention is the disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like.

Primarily the invention relates to the use in disposable articles with high requirements for fluid acquisition, i.e. for uses where relatively high fluid volumes at relatively high flow rates need to be absorbed, such as for disposable baby diapers, articles for severely incontinent adults, training pants and the like. However, the invention can accordingly be applied to devices with relatively lower fluid rates and volumes, such as feminine hygiene devices or articles for light or moderately incontinent adults.

FIG. 1 is a plan view of the diaper 20 in its flat-out, uncontracted state (i.e. with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a liquid pervious topsheet 24; a liquid impervious backsheet 26 joined with the topsheet 24; an absorbent core 28 positioned between the topsheet 24 and the backsheet 26. If not specified differently, the term "upper" refers to the part of a structure directed towards the wearer of the article, "lower" directs away from the wearer FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 22 of the diaper 20. While the topsheet 24, the backsheet 26, and the absorbent core 28 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. patent application Ser. No. 071715,152, allowed, "Absorbent Article With Dynamic Elastic Waist Feature Having A Predisposed Resilient Flexural Hinge", Kenneth B. Buell et al. filed Jun. 13, 1991.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bed-sheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm to about 0.051 mm. Particularly preferred materials for the backsheet include RR8220 blown films and RR5475 cast films as manufactured by Tredegar Industries, Inc. of Terre Haute, IN, US. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26.

The absorbent article may further comprise elastification or closure features well-known in the art and—for example—described in E 0254476 (Alemany).

The specific advantages of the invention result from combining the specific topsheet-and acquisition/distribution materials according to their parameter profile.

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

Generally, the topsheet 24 is compliant, soft feeling, and non-irritating to the wearer's skin. Further, the topsheet 24 is liquid pervious permitting liquids (e.g., urine) to readily penetrate through its thickness. Provided it will satisfy the requirements as laid out later, a suitable topsheet may be manufactured from a wide range of materials, such as porous foams; reticulated foams; apertured plastic films; or woven or nonwoven webs of natural fibres (e.g., wood or cotton fibres), synthetic fibres (e.g., polyester or polypropylene fibres), or a combination of natural and synthetic fibres. There are a number of manufacturing techniques which may be used to manufacture the topsheet 24. For example, the topsheet 24 may be a nonwoven web of fibres spunbonded, carded, wet-laid, meltblown, hydroentangled, combinations of the above, or the like.

Preferably the topsheet according to the current invention comprises a means to adjust hydrophilicity of the material.

In case of nonwoven topsheets, this can be done by adjusting the surface energy of the fibres before the non-woven is formed, or by adjusting the surface energy of the non-woven after it is formed. The hydrophilicity adjustments can be made such that they wash away easily upon wetting such as with urine, or, which is more preferred, such that they remain effective even at repeated wettings, though may be at a reduced level.

Such hydrophilicity adjustments can be incorporated into the resin of the fibres, or can be applied to the fibres just after they are spun, or after the web is formed.

In case of formed and/or apertured films, the surface energy adjustments can evenly also be applied to the resin of the film, or to the surface.

Alternatively, combination composites of both nonwoven and films may be used, and for the hydrophilicity adjustment the respective options of both can be applied.

Also the pore size of the topsheet is of critical importance to the application in the current invention.

Preferably, the topsheet pore size should not be smaller than the pores of the underlaying layer, such that—in combination with the hydrophilicity of both layers—the fluid within the topsheet can be readily drained towards the underlying layer through the hydraulic forces.

In order to further optimize the surface wetness of any topsheets, it has been found advantageous to minimize the volume of fluid which can be retained in the topsheet by minimizing the volume of the topsheet.

However, whilst this can be done by reduction of caliper at constant basis weight (which will result in undesired reduction of pore size—see above) it is more preferred to do so by reduction of topsheet basis weight whilst maintaining (or even enlarging) the pore size.

This basis weight reduction has to be balanced with other mechanical properties, such as strength for maintaining convertability, and also for product integrity during use, or with the ability to retain other materials which might not be bound firmly enough in the core such as particulate superabsorbent materials.

Suitable materials are described in the part showing specific examples, a particularly suitable topsheet is a low basis weight spunbonded material with permanent hydrophilicity at an intermediate level.

Absorbent cores 28 in the meaning of the current invention comprise essentially all absorbent parts of the absorbent article other than the topsheet, which contribute to fluid absorbency or fluid handling.

The absorbent cores should be generally compressible, conformable, non-irritating to the wearer's skin, and capable of absorbing and retaining liquids such as urine and other certain body exudates. As shown in FIG. 1, the absorbent core 28 has a garment surface ("lower" or "bottom" part), a body surface, side edges, and waist edges. In order to fit best into the overall absorbent article design, the absorbent core 28 may be manufactured in a wide variety of overall sizes and shapes (e.g., rectangular, hourglass, "T"-shaped, asymmetric, etc.).

The acquisition/distribution region can be positioned on the absorbent core region such by a layered arrangement as shown in FIG. 1., 29; or it can be partially or completely embedded into the absorbent core structure.

The key element of the current invention can be described by following the fluids flow path after these are released into the absorbent core (i.e. after these penetrated through the topsheet).

For ease of explanation, the absorbent core structure is separated into three functional parts:

First, the absorbent core has to acquire the fluid, i.e. to take up the fluid penetrating through the topsheet at release (gush) rate of the wearer (e.g. at urination rate of the wearer). This is generally (and in particular with high performing absorbent cores) achieved by the acquisition functionality in a specific acquisition region.

Due to the goal of effective use of the materials, the acquisition materials used for this functionality should readily release the fluid to the storage region of the absorbent core, such that it is free to provide void space for acquiring fluid at subsequent gushes.

Examples for acquisition materials are high loft/low density materials, such as synthetic webs with typical densities of less than about 0.08 g/cm 3.

Ultimately, the fluid should be absorbed primarily by the final storage material, where it is absorbed sufficiently strong to remain bound during any further use condition, such as wearing, movement, subsequent gushes etc.

In modern diaper designs, this final storage material very often comprises "superabsorbent material", i.e. mostly hydrocolloid materials forming gels upon wetting.

In order to transfer the fluid effectively to the storage material, an "interim storage and distribution" functionality is required with a "medium fast" fluid pick up rate, which can be less than the one of the acquisition material, but should be faster than the one of the storage material. Thus, it is able to drain the acquisition material before subsequent gushes;

a total interim storage capacity of close to the gush capacity (even at repeated wettings). This should be equal to the gush volume if the initial fluid pick up rate of the final storage medium is very slow compared to gush rates, or accordingly less if the final storage material is able to pick up quicker and starts draining the interim storage material already during the time of the gush a x,y-directional fluid spreading ability which is better than the one of the storage material;

and a fluid release capability to allow final storage medium to drain it.

Whilst this has been described in three functionalities, each of these can comprise sub-layers or regions, or one region may take two of these functionalities at the same time, and might again be a mixture of several primary materials.

As to the fluid transport from one material to another, it is of special interest to keep the fluid transport uninterrupted through undesired resistance at interfaces, such as might occur through lack of wetting and the like. This can be addressed by careful selection of porosity and hydrophilicity properties of adjacent materials, however, it is a further goal of the invention to improve on wetting "bridges" by gradual blending materials of two adjacent regions in a thin mixing layer, through special process steps, such as air-laying at least one of the fibrous components on another porous component, such that the fibres penetrate well into the surface of the other porous material (which may comprise fibres, too) and entangle.

Absorbent cores according to the invention are best made out of several different materials to satisfy the requirements for parameter profiles. Before describing the particularly beneficial combination of such materials, such materials are described in more detail (referring to the physical form they have when being used to form the final absorbent structure ["converted"].

Absorbent Core Materials

Fibrous Materials

The absorbent members for the present invention can comprise fibrous materials to form fibrous web or fibrous matrices. Fibres useful in the present invention include those that are naturally occurring fibres (modified or unmodified), as well as synthetically made fibres. Examples of suitable unmodified/modified naturally occurring fibres include cotton, Esparto grass, bagasse, kemp, flax, silk, wool, wood pulp, chemically modified wood pulp, jute, rayon, ethyl cellulose, and cellulose acetate. Suitable synthetic fibres can be made from polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyolefins such as polyethylene (e.g., PULPEX®) and polypropylene, polyamides such as nylon, polyesters such as DACRON® or KODEL®, polyurethanes, polystyrenes, and the like. The fibres used can comprise solely naturally occurring fibres, solely synthetic fibres, or any compatible combination of naturally occurring and synthetic fibres. The fibres used in the present invention can be hydrophilic, or can be a combination of both hydrophilic and hydrophobic fibres.

For many absorbent members according to the present invention, the use of hydrophilic fibres is preferred. Suitable hydrophilic fibres for use in the present invention include cellulosic fibres, modified cellulosic fibres, rayon, polyester fibres such as polyethylene terephthalate (e.g., DACRON®), hydrophilic nylon (HYDROFIL®), and the like. Suitable hydrophilic fibres can also be obtained by hydrophilizing hydrophobic fibres, such as surfactant-treated or silica-treated thermoplastic fibres derived from, for example, polyolefins such as polyethylene or polypropylene, polyacrylics, polyamides, polystyrenes, polyurethanes and the like. For reasons of availability and cost, cellulosic fibres, in particular wood pulp fibres, are a preferred element for use in the present invention.

Suitable wood pulp fibres can be obtained from well-known chemical processes such as the Kraft and sulfite processes. It is especially preferred to derive these wood pulp fibres from southern soft woods due to their premium absorbency characteristics. These wood pulp fibres can also be obtained from mechanical processes, such as ground wood, refiner mechanical, thermomechanical, chemomechanical, and chemothermomechanical pulp processes. Recycled or secondary wood pulp fibres, as well as bleached and unbleached wood pulp fibres, can be used.

A desirable source of hydrophilic fibres for use in the present invention, especially for absorbent regions requiring both good fluid acquisition and distribution properties, is chemically stiffened cellulosic fibres. As used herein, the term "chemically stiffened cellulosic fibres" means cellulosic fibres that have been stiffened by chemical means to increase the stiffness of the fibres under both dry and aqueous conditions. Such means can include the addition of a chemical stiffening agent that, for example, coats and/or impregnates the fibres. Such means can also include the stiffening of the fibres by altering the chemical structure, e.g., by crosslinking polymer chains.

Polymeric stiffening agents that can coat or impregnate the cellulosic fibres include: cationic modified starches having nitrogen-containing groups (e.g., amino groups) such as those available from National Starch and Chemical Corp., Bridgewater, N.J., USA; latexes; wet strength resins such as polyamide-epichlorohydrin resin (e.g., Kymene® 557H, Hercules, Inc. Wilmington, Del., USA), polyacrylamide resins described, for example, in U.S. Pat. No. 3,556,932 (Coscia et al), issued Jan. 19, 1971; commercially available polyacrylamides marketed by American Cyanamid Co., Stamford, Conn., USA, under the tradename Parez® 631 NC; urea formaldehyde and melamine formaldehyde resins, and polyethylenimine resins. A general dissertation on wet strength resins utilized in the paper art, and generally applicable herein, can be found in TAPPI monograph series No. 29. "Wet Strength in Paper and Paperboard", Technical Association of the Pulp and Paper Industry (New York, 1965).

These fibres can also be stiffened by chemical reaction. For example, crosslinking agents can be applied to the fibres that, subsequent to application, are caused to chemically form intrafibre crosslink bonds. These crosslink bonds can increase the stiffness of the fibres. While the utilization of intrafibre crosslink bonds to chemically stiffen the fibre is preferred, it is not meant to exclude other types of reactions for chemical stiffening of the fibres.

Fibres stiffened by crosslink bonds in individualized form (i.e., the individualized stiffened fibres, as well as process for their preparation) are disclosed, for example, in U.S. Pat. No. 3,224,926 (Bernardin), issued Dec. 21, 1965; U.S. Pat. No. 3,440,135 (Chung), issued Apr. 22, 1969; U.S. Pat. No. 3,932,209 (Chatterjee), issued Jan. 13, 1976; and U.S. Pat. No. 4,035,147 (Sangenis et al), issued Dec. 19, 1989; U.S. Pat. No. 4,898,642d (Moore et al), issued Feb. 6, 1990; and U.S. Pat. No. 5,137,537 (Herron et al), issued Aug. 11, 1992.

In the more preferred stiffened fibres, chemical processing includes intrafibre crosslinking with crosslinking agents while such fibres are in a relatively dehydrated, defibrated (i.e., individualized), twisted, curled condition. Suitable chemical stiffening agents are typically monomeric crosslinking agents including, but not limited to, $C_2$–$C_8$ dialdehyde, $C_2$–$C_8$ monoaldehydes having an acid functionality, and especially $C_2$–$C_9$ polycarboxylic acids. These compounds are capable of reacting with at least two hdroxyl groups in a single cellulose chain or on proximately located cellulose chains in a single fibre. Specific examples of such crosslinking agents include, but are not limited to, glutaraldehyde, glyoxal, formaldehyde, glyoxylic acid, oxydisuccinic acid and citric acid. The effect of crosslinking under these conditions is to form fibres that are stiffened and which tend to retain their twisted, curled configuration during use in the absorbend structures herein. Such fibres, and processes for making them, are described in the above referred patents.

The preferred stiffened fibres that are twisted and curled can be quantified by referencing both a fibre "twisted count" and a fibre "curl factor". As used herein, the term "twist count" refers to the number of twist nodes present in a certain length of fibre. Twist count is utilized as a means of measuring the degree to which a fibre is rotated about its longitudinal axis. The term "twist node" refers to a substantially axial rotation of 180° about the longitudinal axis of the fibre, wherein a portion of the fibre (i.e., the "node") appears dark relative to the rest of the fibre when viewed under a microscope with transmitted light. The twist node appears dark at locations wherein the transmitted light passes through an additional fibre wall due to the aforementioned rotation. The distance between nodes corresponds to an axial rotation of 180°. The number of twist nodes in a certain length of fibres (i.e., the twist count) is directly indicative of the degree of fibre twist, which is a physical parameter of the fibre. The procedures for determining twist nodes and total twist count are described in U.S. Pat. No. 4,898,642.

Preferred stiffened fibres will have an average dry fibre twist count of at least about 2.7, preferably at least about 4.5 twist, nodes per millimeter. Furthermore, the average wet fibre twist count of these fibres should preferable be at least about 1.8, preferably at least about 3.0, and should also preferably be at least about 0.5 twist nodes per millimeter less than the average dry fibre twist count. Even more preferably, the average dry fibre twist count should be at least about 5.5 twist nodes per millimeter, and the average wet fibre twist count should be at least about 4.0 twist nodes per millimeter and should also be at least 1.0 twist nodes per millimeter less than its average dry fibre twist count. Most preferably, the average dry fibre twist count should be at least about 6.5 twist nodes per millimeter, and the average wet fibre twist count should be at least about 5.0 twist nodes per millimeter and should also be at least 1.0 twist nodes per millimeter less than the average dry fibre twist count.

In addition to being twisted, these preferred stiffened fibres are also curled. Fibre curl can be described as the fractional shortening of the fibre due to kinks, twists, and/or bends in the fibre. For the purposes of the present invention, fibre curl is measured in terms of a two dimensional plane. The extent of fibre curling can be quantified by referencing a fibre curl factor. The fibre curl factor, a two dimensional measurement of curl, is determined by viewing the fibre in a two dimensional plane. To determine curl factor, the projected length of the fibre as the longest dimension of a two dimensional rectangle encompassing the fibre, LR, and the actual length of the fibre, $L_A$, are both measured. The fibre curl factor can then be calculated from the following equation:

$$\text{Curl Factor} = (L_A/L_R) - 1.$$

An image analysis method that can be utilized to measure $L_R$ and $L_A$ is described in U.S. Pat. No. 4,898,642. Preferably the stiffened fibres will have a curl factor of at least about 0.30, and more preferably will have a curl factor of at least about 0.50.

These chemically stiffened cellulosic fibres have certain properties that make them particularly useful in certain absorbent members according to the present invention, relative to unstiffened cellulosic fibres. In addition to being hydrophilic, these stiffened fibres have unique combinations of stiffness and resiliency. In particular, the resiliency of these stiffened fibres enables the absorbent member to better maintain its capillary structure in the presence of both fluid and compressive forces normally encountered during use and are thus more resistant to collapse.

Synthetic or thermoplastic fibres can be made from any thermoplastic polymer that can be melted at temperatures that will not extensively damage the fibres. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in absorbent articles, are likely to be stored. The melting point of the thermoplastic material is typically no lower than about 50° C.

The thermoplastic materials, and in particular the thermoplastic fibres, can be made from a variety of thermoplastic polymers, including polyolefins such as polyethylene (e.g., PULPLEX®) and polypropylene, polyesters, copolyesters, polyvinyl acetate, polyamides, copolyamides, polystyrenes, polyurethanes and copolymers of any of the foregoing such as vinyl chloride/vinyl acetate, and the like. Depending upon the desired characteristics for the resulting thermally bonded absorbent member, suitable thermoplastic materials include hydrophobic fibres that have been made hydrophilic, such as surfactant-treated or silica-treated thermoplastic fibres derived from, for example, polyolefins such as polyethylene or polyproppylene, polyacrylics, polyamides, polystyrenes, polyurethanes and the like. The surface of the hydrophobic thermoplastic fibre can be rendered hydrophilic by treatment with a surfactant, such as a nonionic or anionic surfactant, e.g., by spraying the fibre with a surfactant, by dipping the fibre into a surfactant or by including the surfactant as part of the polymer melt in producing the thermoplastic fibre. Upon melting and resolidification, the surfactant will tend to remain at the surfaces of the thermoplastic fibre. Suitable surfactants include nonionic surfactants such as Brij® 76 manufactured by ICI Americas, Inc. of Wilmington, Del., and various surfactants sold under Pegosperse® trademark by Glyco Chemical, Inc. of Greenwich, Conn. Besides nonionic surfactants, anionic surfactants can also be used. These surfactants can be applied to the thermoplastic fibres at levels of, for example, from about 0.2 to about 1 gram per square of centimeter of thermoplastic fibre.

Suitable thermoplastic fibres can be made from a single polymer (monocomponent fibres), or can be made from more than one polymer (e.g., bicomponent fibres). As used herein, "bicomponent fibers" refers to thermoplastic fibres that comprise a core fibre made from one polymer that is encased within a thermoplastic sheath made from a different polymer. The polymer comprising the sheath often melts at a different, typically lower, temperature than the polymer comprising the core. As a result, these bicomponent fibres provide thermal bonding due to melting of the sheath polymer, while retaining the desirable strength characteristics of the core polymer.

Suitable bicomponent fibres for use in the present invention can include sheath/core fibres having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibres for use herein are those having a polypropylene or polyester core, and a lower melting copolyester, polyethylvinyl acetate or polyethylene sheath (e.g., DANAKLON®, CELBOND® or CHISSO® bicomponent fibres). These bicomponent fibres can be concentric or eccentric. As used herein, the terms "concentric" and "eccentric" refer to whether the sheath has a thickness that is even, or uneven, through the cross-sectional area of the bicomponent fibre. Eccentric bicomponent fibres can be desirable in providing more compressive strength at lower fibre thicknesses. Suitable bicomponent fibres for use herein can be either uncrimped (i.e. bent). Bicomponent fibres can be crimped by typical textile means such as, for example, a stuffer boy method or the gear crimp method to achieve a predominantly two-dimensional or "flat" crimp.

In the case of thermoplastic fibres, their length can vary depending upon the particular melt point and other properties desired for these fibres. Typically, these thermoplastic fibres have a length from about 0.3 to about 7.5 cm long, preferably from about 0.4 to about 3.0 cm long. The properties, including melt point, of these thermoplastic fibres can also be adjusted by varying the diameter (caliper) of the fibres. The diameter of these thermoplastic fibres is typically defined in terms of either denier (grams per 9000 meters) or decitex (grams per 10,000 meters). Suitable bicomponent thermoplastic fibres can have a decitex in the range from about 1.0 to about 20, preferably from about 1.4 to about 10.

Fibrous Structures

Said fibrous materials may be used in an individualized form when the absorbent article is being produced, and an airlaid structure is formed on the line. Said fibres may also be used as a preformed web or tissue. These structures are then delivered to the production of the article essentially in endless or very long form (e.g. on a roll, spool) and will then be cut to the appropriate size. This can be done on each of such materials individually before these are combined with other materials to form the absorbent core, of when the core itself is cut and said materials are co-extensive with the core.

There is a wide variety of making such webs or tissues, and such processes are very well known in the art.

Fibre Types

With regard to fibres used for producing such webs, there is nearly no limitation in principle—though certain specific web forming and bonding processes might not be fully compatible with certain materials or fibre types.

Web Forming

When looking at individualized fibres as a starting material for making a web, these can be laid down in a fluid medium—if this is gaseous (air) such structures are generally referred to as "dry-laid", if it is liquid such structures are generally referred to as "wet-laid". "Wet-laying" is broadly used to produce paper tissues with a wide range of properties. This term is most commonly used with cellulosic materials, however, also synthetic fibres can be included.

"Dry-laying" is broadly used for non-woven webs, and often the carding process can be used to form such webs. Also the commonly known "air-laid tissues" fall under this category.

A molten polymer can be extruded into fibres which then can be formed directly into a web (i.e. omitting the process step of making individual fibres which then are formed into a web in a separate process step). The resulting structures are commonly referred to as non-wovens of the meltblown type or—if fibres are significantly more drawn—spunbonded webs.

Further, webs can also be formed by combining one or more of the other formation technologies.

Web Bonding

In order to give certain strength and integrity properties to the web structures, these are generally bonded. The most broadly used technologies are (a) chemical bonding or (b) thermo bonding by melting a part of the web such. For the latter, the fibres can be compressed, resulting in distinct bonding points, which, for example for nonwoven materials, can cover a significant portion of the total area, values of 20% are not uncommon. Or—particularly useful for structures where low densities are desired—"air-through" bonding can be applied, where parts of the polymers (e.g. the sheath material of a BiCo-fibres are molten by means of heated air passing through the (often air-laid) web.

After the webs are formed and bonded, these can be further treated to modify specific properties. This can be—as one of many possible examples—additional surfactant to render hydrophobic fibres more hydrophitic, or vice versa.

Obviously, there is a wide variety of combinations of the fibre types, web forming and web bonding to adjust the properties to the required specification profile. Of particular interest are combined structures where the interface layer between two adjacent with different properties is not a sharp separation line (or plane) but rather a gradual (though thin) transition layer.

Out of the vast variety of such webs, of particular interest for the current invention are:

For the Topsheets

Nonwovens having large pores, a low basis weight (without overly compromising on the strength properties) and an adjustable hydrophilicity. Among other technologies, this could be achieved with materials as exemplified below, i.e. for examples with spunbonded PP nowovens in combination with a permanent surfactant of moderate hydrophilicity. For use in acquisition/distribution regions:

Very low density materials, which—among many other technologies could be achieved by air-laying and subsequent air-through bonding of special eccentric polypropylen core and polyethylene sheath Bicomponent fibres.

Very hydrophilic webs, such as made from natural fibres, especially for storage core structures.

The examples further detailed below will allow to better understand the impact several preferred executions.

The hydrogel-forming absorbent polymers useful in the present invention include a variety of substantially water-insoluble, but water-swellable polymers capable of absorbing large quantities of liquids. Such polymer materials are also commonly referred to as "hydrocolloids", or "superabsorbent" materials. These hydrogel-forming absorbent polymers preferably have a multiplicity of anionic, functional groups, such as sulfonic acid, and more typically carboxy, groups. Examples of polymers suitable for use herein include those which are prepared from polymerizable, unsaturated, acid-containing monomers.

Some non-acid monomers can also be included, usually in minor amounts, in preparing the hydrogel-forming absorbent polymers herein. Such non-acid monomers can include, for example, the water-soluble or water-dispersible esters of the acid-containing monomers, as well as monomers that contain no carboxylic or sulfonic acid groups at all. Examples for such well known materials are described e.g. in U.S. Pat. No. 4,076,663 (Masuda et al), issued Feb. 28, 1978, and in U.S. Pat. No. 4,062,817 (Westerman), issued Dec. 13, 1977.

Hydrogel-forming absorbent polymers particularly useful for the present invention contain carboxy groups. These polymers include hydrolyzed starch-acrylonitrile graft copolymers, partially neutralized starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials for use in making hydrogel-forming particles are slightly network crosslinked polymers of partially neutralized polyacrylic acids and starch derivatives thereof. Most preferably, the hydrogel-forming particles comprise from about 50 to about 95%, preferably about 75%, neutralized, slightly network crosslinked, polyacrylic acid (i.e. poly (sodium acrylate-lacrylic acid)).

As described above, the hydrogel-forming absorbent polymers are preferably slightly network crosslinked. Network crosslinking serves to render the polymer substantially water-insoluble and, in part, determines the absorptive capacity and extractable polymer content characteristics of the precursor particles and the resultant macrostructures. Processes for network crosslinking the polymers and typical network crosslinking agents are described in greater detail in the hereinbefore-referenced U.S. Pat. No. 4,076,663, and in DE-A4020780 (Dahmen).

Preferred hydrogel-forming absorbent polymer particles of the present invention are those which exhibit a high absorptive capacity or Teabag Centrifuge Capacity value.

The superabsorbent materials can be used in particulate form or in fibrous form and may also be combined other elements to form preformed structures.

A broadly known example for such composites are Superabsorbent Material laminates, where superabsorbent particles as described above can be attached to a suitable substrate e.g. by using a suitable glue in a suitable process.

The substrate layer of the laminate can for example be formed by a nonwoven layer or by a tissue layer such as BOUNTY tissue as marketed by the Procter & Gamble Company, or such as a high wet-strength tissue of a basis weight of 22.5 g/m$^2$ as produced by STREPP GmbH & Co, KG, D-5166 Kreuzau-Untermaubach, Germany, under the reference NCB. Alternatively, the substrate layer is formed by a three-dimensional apertured thermoplastic film as described in EP-A- 0 203 820, EP-A- 0 156 471 and EP-A- 0 141 654. Other suitable materials for forming the substrate layer are high wet-strength nonwovens, such as polyolefin nonwovens.

The absorbent gelling material can be attached to the substrate by applying a layer of adhesive to the substrate, followed by deposition of the particles onto the layer of adhesive. A suitable adhesive is for instance hotmelt adhesive as produced by Findley, Roosendaal, the Netherlands under the reference H 2127. The adhesive can be deposited as a melt-blown film which is blown at such high air speeds that the film breaks up into an open network of filaments as described in U.S. Pat. No. 4,573,986. Alternatively, a spiral pattern of adhesive may be deposited to obtain a liquid-permeable network of adhesive filaments as described in U.S. Pat. Nos 3,911,173, 4,031,854, and 4,098,632.

It is also possible to bond the absorbent gelling material without the use of an adhesive. The particles can be deposited onto a moist substrate such that the particles absorb moisture on their surfaces and become tacky. Subsequent drying of the moist substrate under application of pressure, results in attachment of the particles to the substrate.

In case the particles are interconnected by application of an interparticle crosslink agent to form an interpartically crosslinked aggregate, the absorbent gelling material particles may be bonded to the substrate by the interparticle crosslink agent. This has been described in detail in U.S. application Ser. No. 08/142,258 (Hseuh).

A method of forming a multilayer laminate having a multiplicity of tissue layers and layers of absorbent gelling material particles encased between the tissue layers, is described in U.S. Pat. No. 4,578,068. In this structure, the absorbent gelling material particles are bonded to the tissue layers substantially entirely by fibre entrapment. A method for depositing absorbent gelling material particles onto a substrate has been described in U.S. Pat. No. 4,551,191 (Kock).

Other preformed structures can comprise well known air-laid or nowoven composites made of superabsorbent particles or fibres in combination with synthetic fibres and optionally cellulosic fibres.

Absorbent Core structure (specific arrangement of materials)

The following deals with specific arrangements of the various core materials according to the principles already laid out.

The most simple design according to the present invention could be a flat, rectangular layered structure, e.g. combining acquisition material with high pore openings on top of a layer of layers with smaller pore openings on top of a highly absorbent material layer such as Superabsorbent laminates. Wrap sheets in form of tissues or nonwovens can be added for mechanical strength improvements, or superabsorbent containment improvement (e.g. when using particulate materials), or added softness (e.g. on the backsheet side). Of course such added materials or layers must not deteriorate on fluid handling properties, e.g. a wrapsheet between on top of an acquisition material must not have smaller pores and/or be more hydrophobic. In contrast, such material should have properties following the teachings of the present invention.

Such simple layered structures can be made of coextensive layers, or—for efficient use of the materials—such that one or more layers are shorter and/or narrower than others. For example, the acquisition distribution material can be positioned around the loading point of the article, but might be omitted in the rear part of the article. In this case, the well know "cut-slip-process" can be advantageously be used to cut an essentially endless material (e.g. delivered on a roll) such that a shorter patch can be placed on a longer layer underneath—or vice versa.

Other arrangements of different zones can be made by profiling for example on the production line of the absorbent article. This is already broadly used for the making of highly absorbent structures, such as described in Weisman et al. (EP 0 202 125) or Alemany et al. (EP 0 254 476).

In more general terms, the regions with different properties should be arranged such that the gradients referred to in the above (namely decrease of pore size and increase of hydrophilicity and interim storage capacity) direct from the surface of the absorbent article towards the ultimate storage material. Depending on the distribution of the latter, the preferred design can be the layered (Z-profile) structure or a more complex regioned or zoned structure.

The key feature of the invention is to arrange the materials in the most effective way, such that the fluid is drained away from the surface of the absorbent article to the ultimate storage material, without retaining residual moisture in the layer next to the wearers skin, and to do this not only for the first loading but also for subsequent loadings until the design storage capacity of the article is exhausted.

A preferred execution (more detailed in the description of the examples) comprises the following design features:

Underneath a topsheet with specific properties and glued to this is a synthetic acquisition material having large pores.

Then a layer of specially treated cellulosic fibres is arranged (which in a more preferred execution are intermingled with pores of the first layer).

This is then followed by a "storage core", made by current technology of mixing superabsorbent particles with fluff pulp in a profiled "mixed core" with a superabsorbent free "dusting layer" on the backsheet side.

The uppermost synthetic patch has a smaller area than the next treated cellulose layer, which is smaller than the underlying storage core.

For a diaper intended for babies in the range of 8 to 18 kg, also called "MAXI" size, the dimensions for example:

|  | length (x-direction) | width (y-direction) |
|---|---|---|
| total diaper | 450 mm | 330 mm |
| absorbant core | 450 mm |  |
| ear width |  | 230 mm |
| "crotch" |  | 105 mm |
| CS-pulp patch | 100 mm | 250 mm |
| syn.Acq.patch | 75 mm | 400 mm |

Methods/Definitions

General

All tests are carried out at about 23+/−2° C. and at 50+/−10% relative humidity.

Unless specified explicitly, the specific synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na2SO4; 0.85 g/l of (NH4)H2PO4; 0.15 g/l (NH4)H2PO4; 0.19 g/l of CaCl2; ad 0.23 g/l of MgCl2. All of the chemicals are of reagent grade. The pH of the synthetic Urine is in the range of 6.0 to 6.4.

Finished-Product-Acquisition Test

Figure 2:
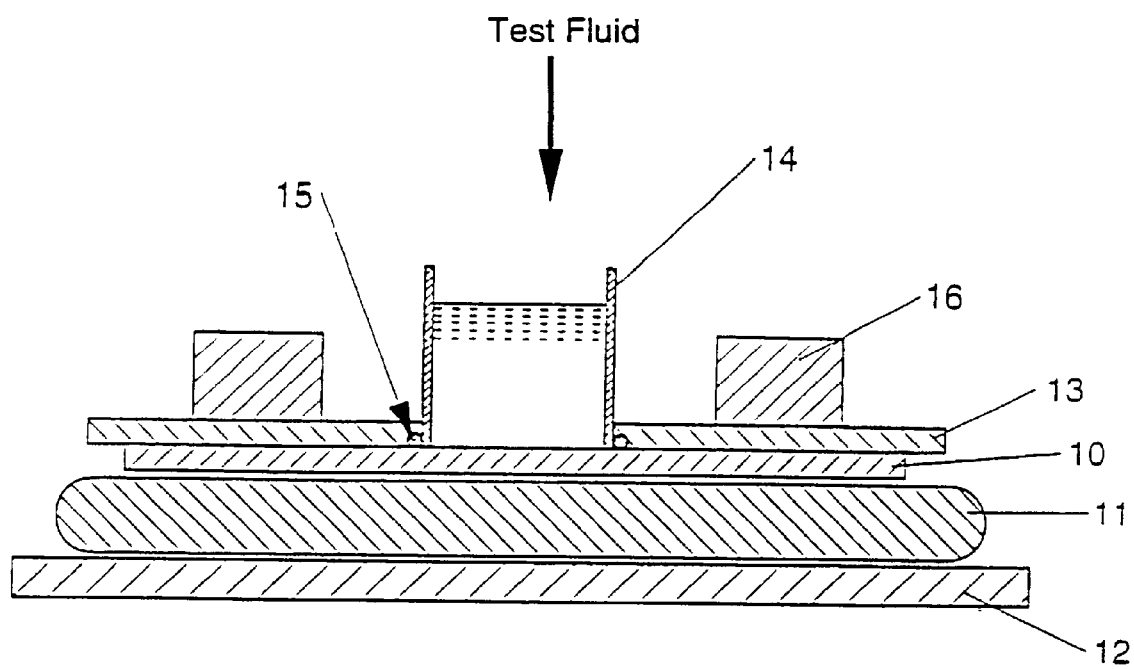
FIG. 2 shows a the key elements of the finished product acquisition test.

Referring to FIG. 2, an absorbent structure (10) is loaded with a 75 ml gush of synthetic urine at a rate of 15 ml/s using a pump (Model 7520-00, supplied by Cole Parmer Instruments., Chicago, U.S.A.), from a height of 5 cm above the sample surface. The time to absorb the urine is recorded by a timer. The gush is repeated every 5 minutes at precisely 5 minute gush intervals until the article is sufficiently loaded. Current test data are generated by loading four formes.

The test sample, which comprises a core and includes a topsheet and a backsheet, is arranged to lie flat on a foam platform 11 within a perspex box (only base 12 of which is shown). A perspex plate 13 having a 5 cm diameter opening substantially in its middle is placed on top of the sample. Synthetic urine is introduced to the sample through a cylinder 14 fitted, and glued into the opening. Electrodes 15 are located on the lowest surface of the plate, in contact with the surface of the absorbent structure 10. The electrodes are connected to the timer. Loads 16 are placed on top of the plate to simulate, for example a baby's weight. A pressure of 50 g cm-2 (0.7 psi) is typically utilised in this test.

As test fluid is introduced into the cylinder it typically builds up on top of the absorbent structure thereby completing an electrical circuit between the electrodes. This starts the timer. The timer is stopped when the absorbent structure has absorbed the gush of urine, and the electrical contact between the electrodes is broken.

The acquisition rate is defined as the gush volume absorbed (ml) per unit time (s). The acquisition rate is calculated for each gush introduced into the sample. Of particular interest in view of the current invention are the first and the last of the four gushes.

This test is primarily designed to evaluate products having an absorbent capacity of about 300 ml to 400 ml. If products with significantly different capacities should be evaluated, the settings in particular of the fluid volume per gush should be adjusted appropriately to about 20% of the theoretical capacity, and the deviations should be recorded.

In Bag Stack Height

Essentially, the in bag stack height is measured by measuring the height of a stack of absorbent products as it is packed into cartons or bags as supplied to the market, and dividing the height by the number of articles in this stack.

It either and most easily can be measured by taking one of the bags and carrying out the measurement, or by simulating the pressure of a packed bag in a suitable device (such as a Stress—strain measurement device such as provided by INSTRON Instruments).

This test has primarily been developed for "bi-folded" products, i.e. products which have only one folding line in the cross (width) direction of the article at about the middle part of the article such that the front and rear part of the article overlay in the bag. For non-folded or tri-folded products (with three layers overlying) the results need to be corrected accordingly.

The Acquisition Drip Test

The drip capacity test described here is based on a standard and industry wide applied raw material test for airfelt (fluff) pulp. The test was initially developed to evaluate the degree to which a fibres can acquire, transport (distribute) away from the loading point and retain a load of synthetic urine in a fibre web. A slight modification of the test is used to simulate more in-use conditions.

In the acquisition-drip test a 75 ml gush of synthetic urine (Jayco as defined above) is applied to a fibre web supported on a wire mesh (porous) at a rate 15 ml/sec. The (saturated) drip capacity is then determined from the fluid that is retained in the fibrous material after the gush.

To execute the test, a sample pad 7.5 cm×25 cm is weighed and placed on a large mesh wire screen positioned on a drip tray (like in the diagram) which is then mounted on a weight balance.

75 ml of Synthetic urine is introduced via a pump (the same pump used and detailed in the acquisition test) into the centre of the sample at a rate of 15±0.25 ml/sec.

By suspending the mesh screen on a balance one can determine closely the amount of urine retained by the sample and urine passed into the drip tray. This helps to minimise variations of the pump delivering the urine. Note the pump delivery rate is confirmed prior to each run.

The drip capacity is then given as the ratio:

Urine retained on saturation (ml)

Dry Weight of sample (g)

Optionally, the "drip time" can be recorded, i.e. the time difference between the start of loading the structure and the time when the first drop falls out of the sample.

Topsheet Evaluations

Repeated-Topsheet-Raw-Material-Strike-Through Test

Strikethrough is the time required for a given volume of liquid applied to a surface to enter through a topsheet material into an underlying absorbent core. The current test is a modification of a industry wide test procedure (EDANA).

The test is executed by carefully cutting a 12.5 cm by 12.5 cm topsheet sample, which is then placed on a simulated core made of 10 pieces of standardized "core replacement" filter paper of 10 cm by 10 cm, supplied by Hollingsworth & Vose, UK of the type ERT FF3.W/S.

The "strikethrough plate" (produced by LENZING AG, Austria) which is connected to an automated timer is placed on the sample.

Three consecutive gushes of test fluid (0.9% saline solution) are applied in one minute intervals to the sample and the respective "strike-through times" are recorded.

Topsheet-on-acquisition-material-wetness Test

This test is used to evaluate the topsheet performance when it is combined not only with a "standard core", but also with an acquisition material.

Three pieces of the "Core replacement" filter paper supplied by Hollingsworth & Vose, UK of the type ERT FF3.W/S of 30.5 cm by 14.0 cm are put underneath a layer of acquisition material (e.g. of the SAT type as exemplified below) of 18 cm by 12 cm. The topsheet sample of also 18 cm by 12 cm is placed upon this.

Then 40 ml of test fluid (JAYCO) (if necessary adjusted for the loading factor of the core replacement filter paper) are added at a rate which avoids overflow of the fluid at the sides of the sample.

A weight of 3.642 kg (8 lbs) is added carefully.

After 15 minutes, the weight increase of the topsheet (after pre-weighing it in the dry state) is measured.

Topsheet-Finished-Product-Wetness Test

After executing the above described Finished-Product-Acquisition test, the topsheet is carefully removed (preferably as complete as possible) from the rest of the product. It is then placed between preweighed pick-up filter paper (supplied by Hollinsworth & Vose, UK, under the designation MEDIUM WHITE W/S) of 7 cm by 10 cm, with 2 sheets underneath and 2 sheets above and a weight of 7.5 kg (on the same area as the filter paper) is added.

After 30 secs the filter paper has drained the topsheet paractically quantitatively, and the fluid retained in the topsheet (wetness) can be measured by re-weighing the filter i.e. paper and determining the difference.

Basis weights are often referred to for various materials. These can be generated by essentially dividing the weight of a specimen by the area of it. The size if the area as well as the number of rewired replicates depend on the homogeneity of the specimen.

Hydrophilicity/-phobicity Definitions

Hydrophilicity (and hence wettability) are typically defined in terms of contact angle and the surface tension of the fluids and solids involved. This is discussed in detail e.g. in the American Chemical Society publication entitled "Contact Angle, Wettability and Adhesion", edited by R. F. Gould, (copyright 1964). In the context of the current invention, materials can be categorized into three groups:

Material which are highly hydrophilic {abbreviated "h+"}. These have generally a contact angle of less than about 80 degree. Examples are cellulosic fibres, or also olefinic polymers when they are treated with effective and strong surfactant (at least when exposed the first time to wetting).

Materials which are "essentially hydrophobic" {abbreviated "hi–"}. These have generally a contact angle of more than about 100 degree. Example are pure olefines (PE/PP) without surfactants (neither at surface, nor resin incorporated).

Material which are "moderately hydrophilic" {abbreviated "ho"}. These have a contact angle of about 90 degree, and examples are PP/PE with less effective resin incorporated surfactants, or other less hydrophilic surfactants applied to the surface of such olefins.

Teabag Centrifuge Capacity Test

The Teabag Centrifuge Capacity test measures the Teabag Centrifuge Capacity values, which are a measure of the retention of liquids in the gelling materials (super absorber) at hydrostatic pressure.

The superabsorbent material is placed within a "teabag", immersed in a 0.9% by weight sodium chloride solution for 20 minutes, and then centrifuged for 3 minutes. The ratio of the retained liquid weight to the initial weight of the dry superabsorbent material is the absorptive capacity of the superabsorbent material.

Two liters of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from Teekanne in Dujsseldorf, Germany. The pouch is heat sealable with a standard kitchen plastic bag sealing device (e.g. VACUPACK2 PLUS from Krups, Germany).

The teabag is opened by carefully cutting it partially, and is then weighed. A 0.200 g+/–0.005 g sample of the superabsorbent material is placed in the teabag. The teabag is then closed with a heat sealer. This is called the sample teabag.

An empty teabag is sealed and used as a blank.

Each teabag is then held horizontally, and the sample teabag is shaken so as to distribute the superabsorbent material evenly throughout the bag. The sample teabag and the blank teabag are then laid on the surface of the saline solution, and submerged for about 5 seconds using a spatula to allow complete wetting (the teabags will float on the surface of the saline solution but are then completely wetted). The timer is started immediately. After 20 minutes soaking time the sample teabag and the blank teabag are removed from the saline solution, and placed in a Bauknecht WS130, Bosch 772 NZK096 or equivalent centrifuge (230 mm diameter), so that each bag sticks to the outer wall of the centrifuge basket. The centrifuge lid is closed, the centrifuge is started, and the speed increased quickly to 1,400 rpm. Once the centrifuge has been stabilised at 1,400 rpm the timer is started. After 3 minutes, the centrifuge is stopped.

The sample teabag and the blank teabag are removed and weighed separately.

The Teabag Centrifuge Capacity (TCC) for the sample of superabsorbent hydrogel-forming material is calculated as follows:

TCC=[(sample teabag weight after centrifuging)–(blank teabag weight after centrifuging)–(dry superabsorbent hydrogel-forming material weight)]÷(dry superabsorbent material weight).

EXAMPLES

Material Descriptions, Abbreviations and Provenance

Before the specific construction of the examples as well as their specific effects and benefits will be detailed, the materials as used for preparation, of the examples will be described in the following:

Toosheet Materials

Reference topsheet material is referred to and supplied by AMOCO GmbH under the trade name of P-10 nonwoven.

It is a conventional thermobonded carded web of about 20 to 22 g/m2, made of PP fibres of about 2.8 dTex dtex and an easily removable surfactant (spinfinish) (i.e. at a first fluid loading, these are very hydrophilic, but at repeated wetting they are essentially as hydrophobic as the base polymer).

Hydrophobic topsheet material are referred to and have been used from FIBERWEB France S.A. under the designation of HOLMESTRA.

They are made of PP fibres by using spunbonding technology, and are not treated with surfactants (hence are essentially hydrophobic as PP). Several fibre coarseness (9, 4.5, and 2.8 dTex respectively) and web basis weights (19 and 18 g/m2 respectively) have been tested.

Materials with a balanced hydrophilicity are referred to and have been used as supplied by COROVIN GmbH, Germany, under the trade name COROSOFT.

They are made of PP fibres by using spunbonding technology. They are treated with a surfactant of the designation HPN, which is less hydrophilic than the one used for the reference materials of FIBERWEB France, and results in an wetting angle of about 90 degr. These surfactants are also more strongly bound to the surface of the fibres in the web, such that the hydrophilicity is maintained over several subsequent loadings.

Several fibre coarseness (9, 4.5, and 2.8 dTex respectively) and web basis weights (19 and 18 g/m2 respectively) have been tested.

Apertured film composites are referred to and have been tested as supplied by PANTEX S.A., Italy.

These are laminated composites, consisting of a layer of about 20 μm PE film between two layers of a conventional spunbonded web of about 14 g/m2, made of PP fibres. The webs are essentially as hydrophobic as PP. The apertures are essentially rectangular holes punched by heated embossing pattern roll through all three layers and cover approximately 16% of total surface (or have such percentage of open area). Two patterns have been tested with 52 holes per $cm^2$ and 38 per $cm^2$ respectively (which consequently are larger in size).

The bonding is achieved through the process of aperturing, where some melting of fibres occurs around the holes.

This material is also disclosed in more detail in EP 0 207 904, assigned to Palumbo.

Acguisition/Distribution Materials

Chemically treated stiffened cellulosic material (CS) supplied by Weyerhaeuser Co., US under the trade designation of "CMC"

Air laid, air through bonded nonwoven {SAT} have been used as made by the applicant on a airlaying and airthrough bonding line, using eccentric, PE sheath/PP core BiCo fibres with a permanent hydrophilizer incorporated into the the PE resin produced by DANAKLON Denmark, under the designation ESEWA.

Webs have been made using two different fibre coarsenesses (3.3 and 6.7 dTex respectively) and basis weights (60 and 90 g/m2) respectively.

The web is disclosed in more detail in WO Patent 94/28838 assigned to Palumbo, the fibres used in EP 0 340 763 assigned to Hansen.

High-loft chemically bonded nonwoven {FT} was supplied by FIBERTECH, North America under the designation type 6852. It is a chemically bonded PET fibre web of a basis weight of 42 g/m2.

High-loft air-through bonded nonwoven {LT} was supplied by LIBELTEX, Belgium, under the designation of Dry-web 50H, made of a blend of PET fibres.

Conventional cellulosic fluff material was supplied by Weyerhaeuser Co., US, under the trade name Flint River. Superabsorbent material was supplied by Stockhausen GmbH, Germany under the trade name FAVOR SXM, using the types "100" and "T5318".

Example Preparation Testing and Results

A key challenge of the recent disposable product developments has been to maintain or even improve acquisition in spite of moving to thinner and thinner products, which generally have less free void space to take up released body fluids.

Table 1 compares a marketed reference product PAMPERS BABY DRY PLUS, produced and sold by Procter & Gamble Co. for example in Germany as Example 1.1 with two thinner alternatives, which differ from the reference 1.1 only in the features as laid out in the table, i.e. in core design and in a tighter packing (resulting in a smaller stack height). Both use significantly less conventional airfelt (−25%), and compensate the loss of absorbent capacity by an increase of Superabsorbent content of an optimized type with a 10% reduced Teabag Centrifuge capacity.

Example 1.2 uses the same acquisition/distribution as used in Example 1.1, namely 5 g of chemically treated and stiffened cellulose {CS}. Example 1.3 replaces this acquisition/distribution layer by 1.8 g of synthetic material of the SAT type (6.7 dTex, 90 gsm).

All three examples have been evaluated for stack height, finished product acquisition performance, and subjectively assessed wet feel.

Essentially, the examples 1.2. and 1.3 reach a significantly lower stack height (i.e. thinner product). Whilst Example 1.2 matches the reference example 1.1 both in acquisition and wetness feel, Example 1.3 outperforms the other two examples in acquisition, but compromises on wetness feel.

In order to further assess these test, a set of different products were made (table 2). The reference 2.1 was essentially the same product as the reference 1.1, however in this test more densified to also have the same stack height as the other products in this comparison of about 8.2 mm. It becomes apparent, that the reference 2.1 looses through this compression in acquisition performance.

The data of this table demonstrate clearly, that by appropriate choice of topsheet and acquisition/distribution material acquisition can be enhanced without negative impacts on topsheet wetness.

In order to be able to distinguish appropriate raw materials in the absence of the impacts of underlying storage cores, the topsheet on synthetic acquisition material test was performed (table 3). It becomes apparent, that materials performing well in the above test show on an average no more than about 0.25 g fluid retained in the topsheet, when placed on top of an appropriate synthetic acquisition/distribution material.

It also becomes apparent, that the hydrophilicty/phobicity balance is an important factor in this surface wetness. However, the good surface wetness results of completely hydrophobic materials (examples 3.6 through 3.8) are counterbalanced by the obvious negatives such materials have on acquisition, such as demonstrated in the strike through test (table 4).

Whilst these tests allowed to assess topsheets as a material for their suitability for this invention, table 5 summarizes data allowing to choose acquisition/distribution materials according to the invention, showing drip capacities of various materials and material combinations. First, when placing a CS material on top of various synthetic materials, drip capacities are in the range of the current invention, however, they are lower than of the sum of the individual materials (i.e. design is functioning as required, however, it does not take full advantage of the benefits). However, when reverting the positioning of these materials, i.e. when placing the CS material underneath the various synthetic materials these negatives are eliminated, and even synergistic effects can be observed. In these cases, we have a particular preferred execution of the acquisition/distribution material of the current invention.

We claim:

1. A disposable absorbent article comprising
a backsheet;
a topsheet;
a fluid acquisition/distribution region;
and at least one fluid storage region;
said article having a total product acquisition performance of more than 3.75 ml/sec at a first gush and more than 0.5 ml/sec at the fourth gush, and a total folded stackheight of less than 9.9 mm per pad, wherein
said topsheet allows to retain no more than 0.25 g of fluid as measured by the topsheet-on-acquisition-material-wetness test, and that fluid acquisition/distribution region has a drip capacity of at least 5.0 grams of fluid per gram material.

2. An absorbent article according to claim 1, further wherein said topsheet comprises nonwoven material with essentially uniform density and porosity.

3. An absorbent article according to claim 1, further wherein said topsheet comprises nonwoven material with non-uniform density and porosity.

4. An absorbent article according to claim 1, further wherein said topsheet comprises apertured film.

5. An absorbent article according to claims 1, further wherein said topsheet comprises fibres with an intermediate hydrophilicity by having a contact angle in the range of 85 deg<theta<100 deg.

6. An absorbent article according to claim 5, further wherein the topsheet fibres maintain the hydrophilicity in the range of 85 deg<theta<100 deg even at repeated insults.

7. An absorbent article according to claim 1, further wherein said topsheet has a Basis weight of less than 15 gsm.

8. An absorbent article according to claim 1, further wherein having one acquisition/distribution region, which is essentially uniform in composition, density and porosity.

9. An absorbent article according to claim 1, further wherein that said acquisition/distribution region is a structure or a composite structure having a hydrophilicity and/or porosity gradient.

10. An absorbent article according to claim 1, further wherein said acquisition/distribution region comprises several sub-regions.

11. An absorbent article according to claim 10, further wherein said acquisition/distribution region comprises one or more sub regions essentially arranged in a layered arrangement.

12. An absorbent article according to claim 1 further wherein said acquisition/distribution region maintains its hydrophilicity even after repeated insults.

13. An absorbent article according to claim 1, further wherein that the acquisition/distribution region has a porosity gradient with decreasing pore size towards the storage core.

14. An absorbent article according to claim 1, further wherein said acquisition/distribution region has a hydrophilicity gradient with increasing hydrophilicity towards the storage core.

15. An absorbent article according to claim 1 further wherein said fluid acquisition/distribution region has a drip capacity of at least 7.0 grams of fluid per gram of material.

16. An absorbent article according to claim 1, further wherein said fluid acquisition/distribution region comprises a composite of synthetic fibrous material placed on cellulose based fibrous material.

17. An absorbent article according to claim 1, further wherein arrangement of said regions is essentially in a layered relation.

18. An absorbent article according to claim 1, further wherein the fluid transport between adjacent regions is enhanced by having at least one thin blending layer between the two regions.

19. An absorbent article according to claim 18, where said blending layer is achieved by air-laying one fibrous material on another porous material.

20. An absorbent article according to claims 1, further comprising backsheet and other mechanical elements to aid use of that article as an disposable, hygienic article.

21. An absorbent article according to claims 1 said article being a diaper, adult incontinence product, feminine hygiene article, or the like.

* * * * *

UNITED STATES PATENT AND TRADEMARK OFFICE
CERTIFICATE OF CORRECTION

PATENT NO. : 6,107,539
DATED : August 22, 2000
INVENTOR(S) : Palumbo et al.

It is certified that error appears in the above-identified patent and that said Letters Patent is hereby corrected as shown below:

Title page,
ABSTRACT,
Line 3, delete "on" and insert therefore -- one --.
Line 7, delete "them" and insert therefore -- than --.

Column 2,
Line 3, between "both" and "cover" delete "-" (the hyphen).

Column 4,
Line 56, between "topsheet" and "and" delete "-" (the hyphen).

Column 7,
Line 20, between "The" and "absorbent" delete "," (the comma).

Column 12,
Line7, delete "hydrophitic" and insert therefore -- hydrophilic --.
Line 27, between "technologies" and "could" insert -- - -- (a hyphen).

Column 13,
Lines 11-12, delete "acrylate-lacrylic" and insert therefore -- acrylate/acrylic --.
Line 21, after "A" insert -- - -- (a hyphen).

Column 15,
Line 18, (in table) delete "absorbant" and insert therefore -- absorbent --.

Column 18,
Line 11, delete "Dujsseldorf" and insert therefore -- Düsseldorf --.
Line 47, after "preparation" delete "," (the comma).
Line 49, delete "Toosheet" and insert -- Topsheet --.

UNITED STATES PATENT AND TRADEMARK OFFICE
CERTIFICATE OF CORRECTION

PATENT NO. : 6,107,539
DATED : August 22, 200
INVENTOR(S) : Palumbo et al.

It is certified that error appears in the above-identified patent and that said Letters Patent is hereby corrected as shown below:

Column 21,
Line 1, delete "stackheight" and insert therefore -- stack height --.

Signed and Sealed this

Thirtieth Day of April, 2002

*Attest:*

JAMES E. ROGAN
*Director of the United States Patent and Trademark Office*

*Attesting Officer*